United States Patent
Boenisch

(10) Patent No.: US 9,030,196 B2
(45) Date of Patent: May 12, 2015

(54) APPARATUS AND METHOD FOR EDDY CURRENT INSPECTION OF TUBULAR COMPONENTS

(75) Inventor: Andreas Boenisch, Schwamstedt (DE)

(73) Assignee: Innospection Group Limited, Jersey (GB)

( * ) Notice: Subject to any disclaimer, the term of this patent is extended or adjusted under 35 U.S.C. 154(b) by 660 days.

(21) Appl. No.: 13/056,288

(22) PCT Filed: Jul. 29, 2009

(86) PCT No.: PCT/GB2009/050940
§ 371 (c)(1),
(2), (4) Date: Mar. 11, 2011

(87) PCT Pub. No.: WO2010/013047
PCT Pub. Date: Feb. 4, 2010

(65) Prior Publication Data
US 2011/0191045 A1  Aug. 4, 2011

(30) Foreign Application Priority Data
Jul. 30, 2008 (GB) .................................. 0813914.9

(51) Int. Cl.
*G01N 27/90* (2006.01)
*G01R 33/12* (2006.01)

(52) U.S. Cl.
CPC ............ *G01N 27/902* (2013.01); *G01N 27/904* (2013.01); *G01N 27/9046* (2013.01)

(58) Field of Classification Search
USPC ................... 324/220–221, 227, 232, 242–243
See application file for complete search history.

(56) References Cited

U.S. PATENT DOCUMENTS

| | | | |
|---|---|---|---|
| 4,292,589 A * | 9/1981 | Bonner | 324/221 |
| 4,855,676 A * | 8/1989 | Cecco et al. | 324/220 |
| 6,281,678 B1 | 8/2001 | Auville | |
| 2003/0057943 A1 | 3/2003 | McClelland | |
| 2009/0166035 A1 * | 7/2009 | Almaguer | 166/254.1 |

FOREIGN PATENT DOCUMENTS

| | | |
|---|---|---|
| DE | 4118406 A1 | 12/1991 |
| DE | 19714685 A1 | 10/1997 |
| DE | 19726513 A1 | 1/1999 |
| GB | 2245071 A | 12/1991 |
| JP | 10318987 A | 12/1998 |

(Continued)

OTHER PUBLICATIONS

H.M. Sadek; NDE technologies for the examination of heat exchangers and boilder tubes-principles, advantages and limitations; Insight vol. 48, No. 3, Mar. 2006.*

(Continued)

*Primary Examiner* — Jay Patidar
(74) *Attorney, Agent, or Firm* — Sunstone IP

(57) ABSTRACT

A method and apparatus for the non-destructive testing of electrically conductive components such as wellbore tubulars, which is suitable for testing the components in situ a wellbore installation. The method comprises the steps of performing a remote field eddy current test phase and at least one of a conventional direct-field eddy current test phase and a partial saturation eddy current test phase. A measurement data set from each of the test phases is obtained and the combined measurement data is processed to evaluate a condition of the test component.

22 Claims, 7 Drawing Sheets

(56) References Cited

FOREIGN PATENT DOCUMENTS

WO        2006113504  A2     10/2006
WO    WO 2008090370  A2  *   7/2008

OTHER PUBLICATIONS

International Search Report dated Nov. 24, 2009 from PCT Patent Application No. PCT/GB2009/050940 filed Jul. 29, 2009 (3 pages).

Written Opinion dated Nov. 24, 2009 from PCT Patent Application No. PCT/GB2009/050940 filed Jul. 29, 2009 (7 pages).

International Preliminary Report on Patentability dated Feb. 1, 2011 from PCT Patent Application No. PCT/GB2009/050940 filed Jul. 29, 2009 (8 pages).

* cited by examiner

APPARATUS AND METHOD FOR EDDY CURRENT INSPECTION OF TUBULAR COMPONENTS

The present invention relates to non-destructive testing, and in particular to an improved method and apparatus for the inspection of components, including tubular components used in the oil and gas exploration and production industries.

Non-destructive testing techniques are known for the detection and identification of defects and/or fatigue in the external wall of tubular components used in the oil and gas industry, such as casings, production tubing, and pipelines.

Ultrasound inspection techniques are typically used in the inspection of tubular components, for example as described in U.S. Pat. No. 4,162,635. The ultrasound signal is transmitted into the tubing wall, and analysis of the signal reflected from the opposing wall allows information on the wall thickness to be derived. A number of different ultrasonic tools and methods are available, but there are drawbacks and deficiencies associated with their operation. Firstly, ultrasonic tools operating according to the contact method require good coupling between the contact transducers and the test object, and the large mismatch in the acoustic impedance of air and the acoustic impedance of the test material must be overcome. This requires the use of a couplant, for example a liquid or gel-like material that has a low acoustic impedance mismatch and therefore good acoustic coupling between the transducers and the tubular. Couplant variations create inconsistencies in the measured data, and in some test environments (such as high temperature environments) there may be significant difficulties associated with achieving appropriate couplant distribution and consistency, and difficulties in preventing degradation of the couplant material. It may not be possible to provide couplant at all in some test environments, for example in the interior of pipelines or downhole.

Ultrasonic inspection tools are also highly sensitive to dirt and debris, which can interfere with the acoustic coupling and/or show up as anomalous features or artefacts in the analysed data. This means that ultrasonic inspection may not be practicable for some wellbore environments. In particular, it may not be usable for tubulars which cannot be cleaned by pigs, for example those with small inner diameter, internal restrictions and/or low pressure or flow rates. In addition, some pipelines are not piggable due to limited access points for the launch and retrieval of pigs. In many instances, unpiggable lines are more prone to corrosion due to difficulties in treating the lines with anti-corrosion fluids. This presents the industry with challenges. Operators and installation managers in many jurisdictions are now required to implement full pipeline inspection programmes, with previously used impact tests or hammer tests often considered to be insufficient for proper inspection of tubulars.

Many tubular components used in the oil and gas industry, including casings, production tubing and pipelines, are exposed to highly corrosive fluids during wellbore construction and production phases of the well. Although high cost corrosion-resistant materials such stainless steel or titanium have been used in some downhole applications, it is preferable to reduce construction costs by using lower grade steels where possible. To resist corrosion of the metal components, spray-on coatings may be applied to surfaces which are exposed to corrosive fluids. A variety of coatings are available including solid films, powder coatings and paints, with the coating selected depending on the particular application.

Advanced lining systems have been developed to prevent the corrosion of tubulars, which comprises a separate tubular liner made from a non-corrosive material which fits inside the metal tubular. One such example is the lining system marketed under the Duoline® trade mark, which provides a liner formed from a corrosion resistant material such as glass-reinforced-epoxy (GRE) or polyvinyl chloride (PVC) inside a steel pipe. A fibre glass epoxy liner is typically set into tubing with a cement grout. Connections between adjacent tubing sections are positioned around every 12 meters of the tubular, and consist of a special coupling including a corrosion barrier ring and flares which engage the liners. Lining systems offer improved durability when compared with spray-on coatings.

A disadvantage of lined tubular systems is the difficulty they present in using conventional inspection techniques to identify defects and/or fatigue in the external wall of the tubular. For example, ultrasonic inspection tools are unsuitable for the internal inspection of lined pipes, as the liner and cement grout create stand-off between the ultrasonic transducers and the tubing wall. Even if acoustic coupling between the test object and the transducers were achievable, the analysis would be complicated by the presence of multiple layers with differing acoustic characteristics.

Remote-field (or far-field) eddy current testing, commonly referred to as RFT, RFEC or RFET, was developed in the 1960s for inspecting pipe and tubing. An RFET system uses an excitation coil placed inside and co-axially with a pipe. An alternating current, typically with a frequency of the order of 500 Hz or less, drives the coil to produce an associated alternating magnetic field. In RFET operation, the eddy currents produced in the tubular extend axially in the tubular wall. The magnetic field from the eddy currents may extend further axially along the tubular compared with the magnetic field produced by the excitation coil. The exciter field is dominant in an area near the exciter coil, but the eddy current field becomes dominant at some distance away from the exciter coil. By positioning receiving coils at a distance where the magnetic field from the eddy currents is dominant, they are substantially unaffected by the direct field from the exciter coil, but can still adequately measure the field strength from the eddy current magnetic field. The strength of the eddy current magnetic field at this distance from the excitation coil is weak, but it is sensitive to changes in the tubular wall from the inner diameter and the outer diameter. Sensors are typically placed adjacent to the pipe wall at a distance from the exciter of around 2 to 3 times diameter of the pipe. At this distance, direct coupling between the excitation coil and the detectors is negligible, and the detectors are sensitive to the response of the pipe in the area of the detectors. When appropriate conditions are met, changes in the phase of RFET receiver signal with respect to the phase of the exciter voltage are directly proportional to the changes in the wall thickness within the inspection area. Localised changes in wall thickness result in phase and amplitude changes, and these changes are indicative of defects including cracks, corrosion pitting or thinning due to corrosion or erosion.

RFET tools are capable of operating in an absolute mode and a differential mode. In an absolute mode, a change in the condition of the test object appears as a change in the electrical impedance of the test coil. By measuring this absolute change in impedance, much information can be gained about the test object. In an absolute mode, the RFET test unit can be used for conductivity analysis lift-off measurements, material property changes and thickness measurements. In a differential mode, two detector coils are provided which may be wound in opposition. When the two coils are detecting an area of the test object which does not contain any flaws, there is no differential signal developed between the coils because they are both inspecting identical material. However, when one coil is located over a defect and the other is over good material, a differential signal is produced between the coils. The RFET tool in its differential mode is therefore very sensitive to localised defects, but is insensitive to slowly varying properties such as gradual dimensional and temperature changes. Examples of RFET probes and methods are described in DE 19714685 A1 and EP 0905497.

RFET testing is a useful technique for the inspection of pipelines, and in particular has high sensitivity and is useful for detecting general wall loss. However, RFET does not provide a complete solution. One drawback of RFET is that it is not able to differentiate between signals from inner and outer surfaces of tubular being inspected. In order to detect local defects, damage to connectors or couplings, and to analyse coating thickness, different inspection techniques are required.

One aim and object of the invention is to provide a method and apparatus which overcomes or mitigates the drawbacks of prior art non-destructive testing techniques. A further aim and object of the invention is to provide an alternative method and apparatus to those proposed in the prior art. Additional aims and objects will become apparent from reading the following description.

SUMMARY OF THE INVENTION

According to a first aspect of the invention there is provided a method for the non-destructive testing of electrically conductive components, the method comprising the steps of:
  performing a remote field eddy current test phase on a test component;
  performing at least one additional test phase on the test component, selected from the a conventional eddy current test phase and a partial saturation eddy current test phase;
  obtaining a measurement data set from each of the test phases, each measurement data set comprising measurement data corresponding to a plurality of test positions;
  combining the measurement data sets in a data processing means and processing the combined measurement data to evaluate a condition of the test component.

In the context of this description, the term partial saturation eddy current refers to an eddy current testing technique in which applied magnetic field lines are used in combination with an eddy current signal. This terminology is known in the art, but may also be referred to as magnetic biased or DC field biased eddy current testing.

The method may comprise the additional step of selecting or rejecting the test object for further use according to the evaluated damage condition. Alternatively, the method may comprise the step classifying the test object according to the evaluated damage condition. A tubular may for example be classified for a lower grade of use or approved for a particular application.

The test component may be rejected if a limit value is exceeded in one of the at least two test phases.

According to one embodiment, a comparison of measurement data from the at least two test phases at a test position is performed by the data-processing means on the test object when evaluating the damage condition. Thus the method involves verifying a potential damage condition at a particular location by correlating the data with data obtained from another of the test phases. This offers the advantage that an event which is not clearly indicated as a defect by one test phase (for example due to the test phase being deficient at indicating a category of defect) can be cross-referenced to measurement data from the other test phases. This allows more accurate determination of marginal damage conditions, without relying on the interpretation of an operator of the test equipment.

The method has particular application to pipelines or tubular which are lined, cladded or coated with an electrically insulating material. Thus, according to an aspect of the invention there is provided a method of non-destructive testing of tubular components of a wellbore or pipeline installation in situ in the wellbore installation, the wellbore or pipeline installation having at least one section lined with an electrically insulating material, the method comprising the steps of:
  performing a remote field eddy current test phase on a test component;
  performing at least one additional test phase on the test component, selected from the a conventional eddy current test phase and a partial saturation eddy current test phase;
  obtaining a measurement data set from each of the test phases, each measurement data set comprising measurement data corresponding to a plurality of test positions;
  combining the measurement data sets in a data processing means and processing the combined measurement data to evaluate a condition of the test component.

Embodiments of the second aspect of the invention may comprise essential, preferred or optional features of the first aspect of the invention as herein defined.

According to a third aspect of the invention, there is provided a method for the non-destructive testing of tubular components made of electrically conductive material, the method comprising the steps of:
  deploying an inspection tool system in a pipeline system, the inspection tool system comprising a remote field eddy current testing apparatus and at least one testing apparatus selected from a conventional eddy current testing apparatus and a partial saturation eddy current testing apparatus, and;
  performing at least two different test phases on the pipeline system during a single trip of the inspection tool.

The pipeline system may be a wellbore tubular, and in particular may be wellbore casing or a wellbore liner. The inspection tool may be deployed to a downhole location from surface. In a preferred embodiment, the wellbore tool is deployed on an umbilical. Measurement data may be transmitted to surface via the umbilical.

According to one embodiment of the invention, the method includes the steps of:
  performing a remote field eddy current test phase;
  performing a conventional eddy current test phase;
  performing a partial saturation eddy current test phase.

The method may include the additional step of combining measurement data sets from at least two of the test phases to provide a combined measurement data set. The combined measurement data set may be processed to evaluate a condition of the pipeline system.

The data may be transmitted to surface for processing and/or interpretation. Preferably, the data are transmitted to surface in real time.

According to a fourth aspect of the invention, there is provided a method of evaluating a condition of a test object, the method comprising the steps of:
  Receiving measurement data sets from at least two test phases performed on a test component including a remote field eddy current test phase and at least one of a conventional eddy current test phase and a partial saturation eddy current test phase;
  Combining the measurement data sets obtained from the test phases;

Processing the combined measurement data to evaluate a condition of the test component.

According to a fifth aspect of the invention, there is provided an inspection tool system for the non-destructive testing of tubular components, the inspection tool system comprising a remote field eddy current testing apparatus and at least one testing apparatus selected from a conventional eddy current testing apparatus and a partial saturation eddy current testing apparatus, and a data processing module configured to process combined data from at least two measurement data sets obtained from the different testing apparatus.

The tool system may comprise at least one downhole tool module configured for location inside a wellbore tubular test component. Equally the tool system may comprise at least one pipeline tool module configured for location inside a pipeline tubular test component.

According to a sixth aspect of the invention, there is provided an apparatus for the non-destructive testing of tubular components, the apparatus comprising testing apparatus configured to perform a remote field eddy current test and a partial saturation eddy current test. The apparatus may also be configured to perform a conventional eddy current test.

According to a seventh aspect of the invention, there is provided a computer program product bearing machine readable instructions for implementing the method according to the fourth aspect of the invention.

According to an eighth aspect of the invention, there is provided a computer apparatus loaded with machine readable instructions for implementing the method of the fourth aspect of the invention.

Embodiments of any of the second to ninth aspects of the invention may comprise essential, preferred or optional features of the first aspect of the invention as herein defined.

Preferably, the first, second, third, fourth or fifth aspects of the invention comprise the additional step of generating a report on the condition of a test component. The methods may comprise the additional step of using the evaluation of the condition of a test component to generate a display to a user. The methods may comprise the additional step of using the evaluation of the condition to create an image of the condition of the test object and displaying the image to a user.

The invention extends to reports, images and data sets generated by or from the methods of the first to fifth aspects of the invention.

According to a ninth aspect of the invention, there is provided a method for the non-destructive testing of tubular components made of electrically conductive material, the method comprising the steps of:
performing at least two different test phases on a test object, the test phase selected from the group comprising conventional eddy current testing, partial saturation eddy current testing, and remote field eddy current testing;
obtaining a measurement data set from each of the at least two different test phases, each measurement data set comprising measurement data corresponding to a plurality of test positions;
combining the measurement data sets in a data processing means and processing the combined measurement data to evaluate a condition of the test object.

To aid an understanding of the invention, example embodiments will now be described with reference to the following drawings, of which:

Figure 1:
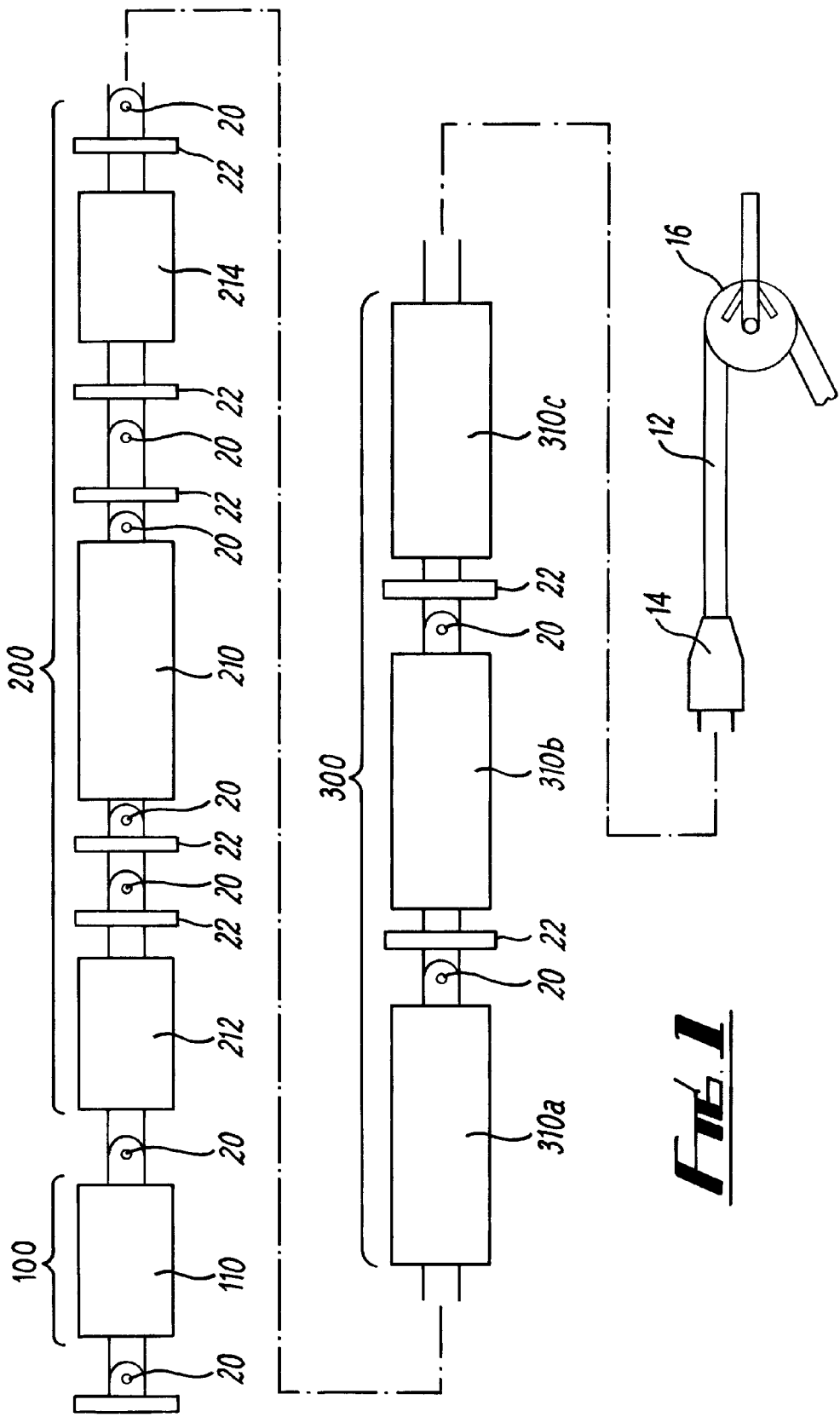
FIG. 1 is a schematic representation of an inspection tool system in accordance with an embodiment of the invention.

Referring firstly to FIG. 1, there is shown a pipeline inspection tool system, generally depicted at 10, comprising an eddy current detection subsystem 100 consisting of conventional eddy current testing and partial saturation eddy current testing apparatus, and a remote field eddy current testing (RFET) subsystem 200. Associated electronic components, including a fibre optic module, AC/DC converters, AC/AC transformers, DC power supplies, power supply control modules, microprocessors, data storage modules, multiplexers, and amplifiers are included in the electronics subsystem shown generally at 300. The tool system 10 is connected to an umbilical 12 via a suitable umbilical termination 14. The tool system 10 is configured for the inspection of downhole tubular installations, such as wellbore casings or liners. The umbilical 12 passes through a sheave 16 located at surface on a platform (no shown). The sheave 16 comprises an encoder system (not shown) which allows the depth of the tool to be precisely determined, and therefore permits depth registration of the data measured by the tool system. The depth registration data is used in the analysis of test data. The eddy current testing subsystem 100, the RFET subsystem 200 and the associated electronics subsystem 300 are axially separated along the length of the tool system 10. In this embodiment, the eddy current testing subsystem 100 is provided at a downhole or distal end of the tool system 10, and the electronics subsystem 300 is provided on an uphole or proximal end of the tool system 10, with the RFET subsystem 200 disposed in between. It will be appreciated that other arrangements of components of the tool system 10 are within the scope of the invention.

Individual modules of the subsystems 100, 200, 300 are connected to one another by universal joints 20 to allow relative rotation and pivoting of joined components. A plurality of wheeled centraliser subs 22 are axially spaced along the tool system. The wheeled centraliser subs 22 provide centralisation of the tool components and facilitate passage through the inspected tubular.

The tool system 10 is exposed to corrosive fluids, including hydrocarbons and brine, and is formed from a suitably non-corrosive material such as stainless steel.

Figure 2:
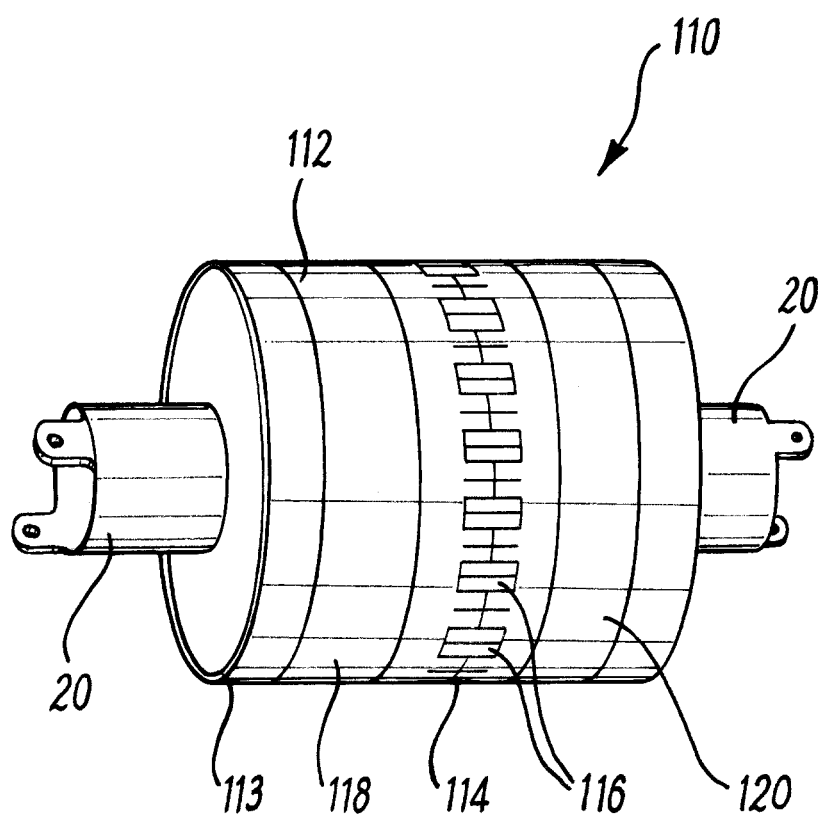
FIG. 2 is an enlarged view of an eddy current testing module of the embodiment of FIG. 1.

FIG. 2 is an enlarged view of the eddy current testing module 110. The module comprises a substantially cylindrical body 112 with universal joints 20 mounted at respective opposing ends. The module 110 has components formed of a ferromagnetic material, and to avoid contact with the inner surface of the inspected tubular, it is provided with a protective coating. In this embodiment, a neoprene layer 113 is baked on to the outer surface of the module 110 to prevent the carbon steel used in the module coming into contact with the inspected pipe.

The module 110 is configured for partial saturation eddy current testing. The module 110 comprises an array 114 of eddy current sensors 116 located approximately centrally between poles 118, 120 of an electromagnet. The sensor array 114 provides complete annular coverage of the tubular. The individual sensors have a width in the range of 5 mm to 30 mm, and are positioned at a distance from the inner surface of the tubular to achieve the required balance between sensitivity and fluid bypass. The module 110 also comprises an exciter coil (not shown) for producing an eddy current in the material between the electromagnet. In an alternative embodiment, a permanent magnet system capable of inducing sufficient field strength is used instead of the electromagnet.

The electromagnet is arranged to apply DC field lines to the tubular in the volume radially adjacent the sensor array 114, and is adjustable to control the field strength to allow for particular tubular material and wall thickness. Adjacent tool modules may include wheeled centraliser subs 22 to centralise the module 110 in the tubular being inspected. The magnets and eddy current sensors are held at a constant distance from the surface of the tubular by the subs 22. The basis of the partial saturation eddy current testing technique is that when a defect is present, the magnetic field due to the applied direct current field has a higher flux density, which causes a change in the relative magnetic permeability in the tubular. This affects the induced eddy current field in the tubular wall, which is detected by the eddy current sensor array 114.

In this embodiment, the module 110 comprises an array of eddy current sensors 116 positioned in two rings in such a way that complete coverage of the inside of the tubular is achieved by the two rings. The module 110 is operable in a differential mode, which is highly sensitive to localised defects in the tubular. The module 110 may also be selectively operable in an absolute mode. However, since partial saturation eddy current testing is principally a measurement of relative changes in permeability, in practice the technique is most useful in the differential mode, used to detect and analyse localised defects such as small pits and flaws.

The sensors are connected by cables to the electronic subsystem 300 via cables (not shown). The signals from the sensors are received in a multichannel multiplexer housed in electronic chamber 310a, and the respective measurement data are acquired and position-registered. The measurement data are transmitted to surface in real time via a fibre-optic interface and multiplexer housed in electronic chamber 310c, and the fibre optic line contained in the umbilical 12. At surface, the measurement data are received in a data processing module for recording, and subsequent processing and analysis.

The partial saturation eddy current testing technique allows external and internal defects to be differentiated. It is also a relatively fast technique, as frequencies of the order of 10 kHz to 150 kHz (preferably in the range of 50 kHz to 100 kHz) can be used. Harmonics of the selected frequency may also be used in a multiple frequency mode (for example two to four simultaneous frequencies) for selective analysis of indications. The analysis of signal phase and signal amplitude allows characterisation of defects and evaluation of the condition of the tubular.

The module 110 is also capable of performing a conventional eddy current test, using the same components with the electromagnet deactivated. The conventional eddy current test phase could be performed over the whole of or a specified region of the tubular, as an alternative to the partial saturation eddy current test. Preferably though, the tool system is used to perform a partial saturation eddy current test and a conventional eddy current test on the same tubular. The test phases may be performed sequentially, for example one on run-in and one on pull-out of the tool system, and thus two tests may be performed on a single trip. In an alternative embodiment, the tool system comprises an additional module which performs conventional eddy current testing simultaneously with the partial saturation eddy current test phase performed by the module 110. The additional module may be identical to the module 110, and may be capable of performing partial saturation eddy current testing and conventional eddy current testing to provide the system with redundancy and/or flexibility of operation. Three test phases may therefore be performed on a single trip.

The module 110 is capable of performing conventional eddy current testing in differential and absolute modes. The module may therefore operate in an absolute mode in order to provide a measurement of gradual changes in the condition of the tubular, such as changes to wall thickness caused by erosion.

Referring again to FIG. 1, the RFET subsystem 200 comprises an RFET current sensor module 210, disposed between exciter coils 212, 214. The spacing between the sensor system and the exciter coils is approximately equal to 2.5 to 3 times the inner diameter of the tubular. This is the optimal distance for detecting remote field effects due to the magnetic field lines which penetrate the tubular and are detected by the far field sensors, with negligible sensitivity to direct field lines from the excitation coils. Either or both exciter coils 212, 214 may be used to produce the remote eddy current field which is detected by the sensor module 210. This provides for flexibility of use; the two exciter coils may be operated together to increase the strength produced eddy current magnetic field in the area of the sensors. The RFET module operates in a frequency range of approximately 10 Hz to 1 kHz.

The RFET subsystem 200 is operable in an absolute mode and a differential mode. In the absolute mode, the system is optimised for the detection of gradual defects and/or wall thinning. Phase shift measured by the RFET subsystem 200 and is directly proportional to wall loss, and amplitude is indicative of defect volume. In differential mode, the system is optimised for the detection of localised defects.

Figure 3:
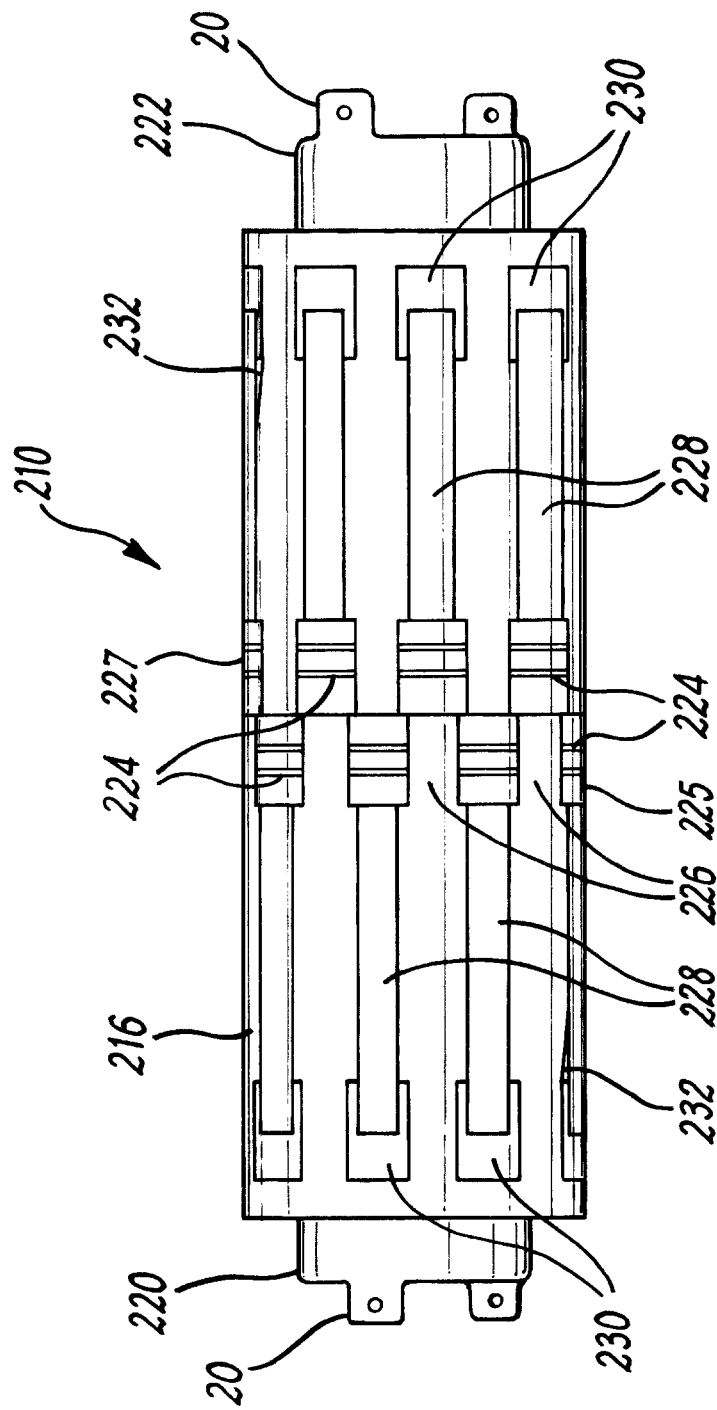
FIG. 3 is an enlarged view of a Remote Field eddy current sensor module of the embodiment of FIG. 1.

FIG. 3 is an enlarged, side-view of the remote field eddy current sensor module 210. The module 210 comprises a substantially cylindrical tool body 216, with universal joints 20 mounted at opposing ends 220, 222, and coupled to adjacent tool sections. The adjacent tool sections are provided with wheeled centraliser subs 22 which centralise the sensor module 210 within the inspected tubular. The module 210 comprises multiple sensors 224 circumferentially separated on the tool body 216. The module comprises a first ring 225 of sensors 224 on the body, with the individual sensors 224 separated by gaps 226. A second ring 227 of sensors is located in an axially separated position, and the circumferential locations of the sensors in the second ring correspond to the gaps in the first ring such that complete circumferential coverage is provided by the two rings of sensors. The sensors are mounted on respective arms 228 which extend longitudinally on the body. The arms 228 are pivotally mounted on bosses 230 positioned towards the first and second opposing ends 220, 222 of the body 216. Actuators 232 are provided for maintaining the arms in radially outward position, by pivoting the arms from their respective connected ends. Actuation can move the sensors radially outwards into contact with the inner surface of the tubular being inspected to achieve the highest possible sensitivity. In one embodiment, the arms are spring-loaded to be biased towards an extended position, and forces imparted by obstacles or curved sections of the tubular caused the receivers to temporarily retract. In other embodiments, the actuators may comprise powered systems for controlled extension or retraction of the arms and sensors.

In this embodiment, the sensors include two pairs of transducers to allow the apparatus to be selectively operated in the differential mode. The sensors of the RFET subsystem 200 are connected by cables to the electronic subsystem 300 via cables (not shown). The detected signals are of low amplitude, and lock-in amplifiers (not shown) allow the extraction of the signal phase and amplitude from the noisy raw signal. The signals are received in a multichannel multiplexer housed in electronic chamber 310a, and the respective measurement data are acquired and position-registered. The measurement data are transmitted to surface in real time via a fibre-optic interface and multiplexer housed in electronic chamber 310c, and the fibre optic line contained in the umbilical 12. At surface, the measurement data are received in a data processing module for recording, and subsequent processing and analysis.

Figure 4A:
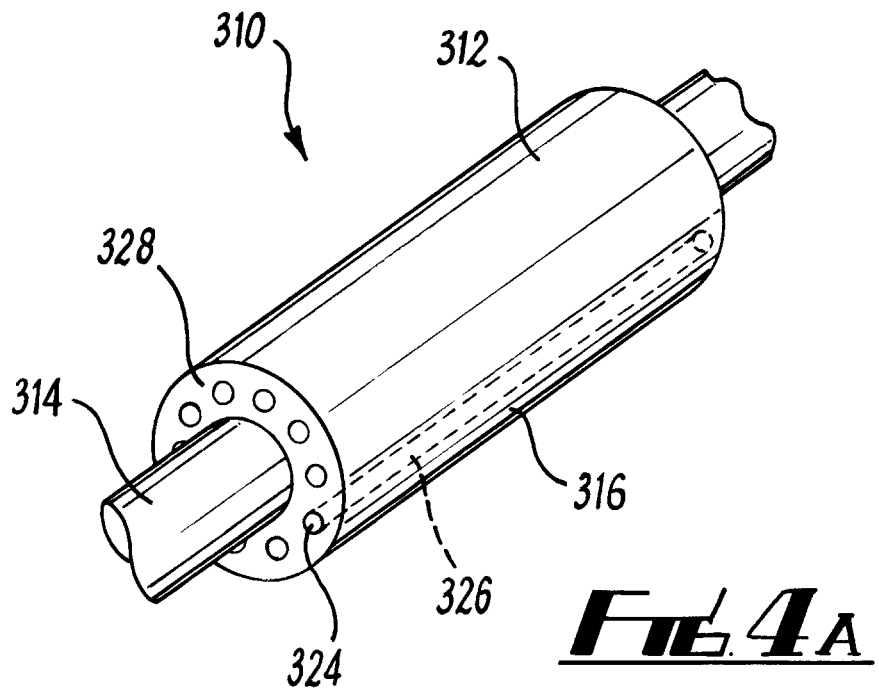
FIGS. 4A and 4B are respectively perspective and cross-sectional views of an electronics chamber of the embodiment of FIG. 1.
Figure 4B:
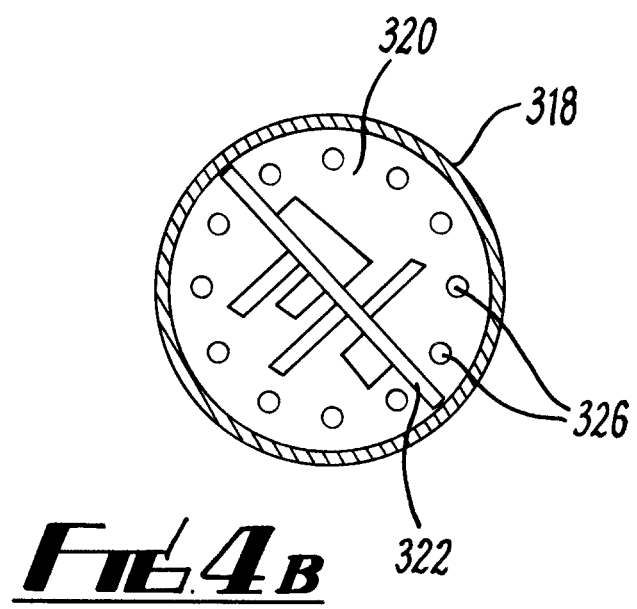

FIGS. 4A and 4B show an example of an electronics chamber 310, forming part of the electronics subsystem 300. The chamber 310 comprises a tubular body 312 comprising a first diameter section 314 which is coupled to adjacent tool modules, and an enlarged diameter section 316. The enlarged diameter section 316 is upstanding from the first diameter section 314, and is formed to an outer diameter which approaches the maximum outer diameter of the tool system 10. The chamber 310 is preferably formed from a non-corrosive material such as stainless steel.

The outer surface 318 of the electronics chamber 310 is centralised within the inspected tubular by respective wheeled centralisers 22. The electronic chamber 310 is formed to be close to the maximum outer diameter of the tool, to provide a large internal volume 320 for housing the electronic boards 322 and components. The annular space between the outside of electronic chamber and the inner surface of the inspected tubular is therefore small, and fluid flow through the annular space is restricted. In order to allow adequate fluid flow and pressure differentiation from upper and lower sides of the electronics chamber 310, a number of fluid paths 324 are provided in the chamber 310. In this example, and as best illustrated in FIG. 4B, the fluid paths are provided by tubular bypass conduits 326 which are formed to extend through the volume 320 defined by the outer surface of the chamber. The conduits are formed from metal (e.g. stainless steel) tubes which are sealed with the respective end walls 328 of the chamber. The flow paths 324 are therefore isolated from the inside 320 of the chamber. Although the conduits reduce the internal volume of the chamber, this arrangement allows components such as electronic circuit boards with a diameter up to the inner diameter of the chamber to be housed. This is convenient for the design of the electronic circuit boards in the apparatus. In other embodiments, bypass flow channels 324 may be formed in the outer surface 318 of the tubular. However, the arrangement shown in FIGS. 3A and 3B has the advantage that circular seals can be used.

In the illustrated embodiment, the chamber 310a houses various electronic components including those required for pre-processing the measured signals. Chamber 310b contains a DC power supply and corresponding control system, and a lock-in amplifier for extraction of the measured signals from associated signal noise. Chamber 310c contains an AC/DC converter, an AC/AC transformer, and a fibre optic interface which allows the measured data to be transmitted to surface via the umbilical 12. It will be understood that alternative arrangements of the electronics system are within the scope of the invention.

Figure 5:
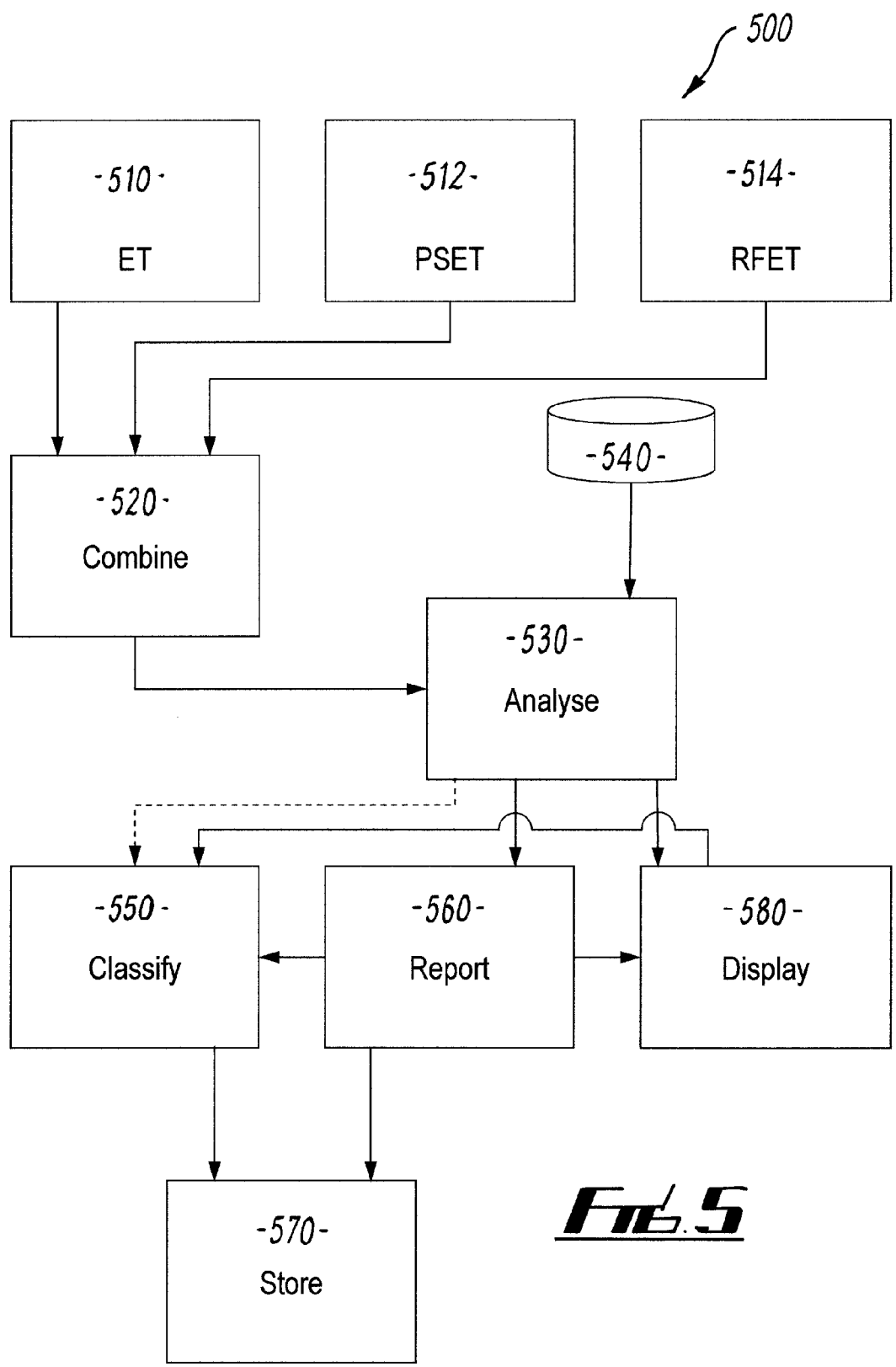
FIG. 5 is a block diagram schematically showing the interaction of components of the apparatus of FIG. 1 in overview.

FIG. 5 shows schematically the interaction 500 of different components of the tool system 100. At steps 510, 512, 514, the eddy current testing (ET) phase, the partial saturation eddy current testing (PSET) phase, and the remote field eddy current testing (RFET) phase, are performed. The tests may be performed sequentially in any order, or two or three of the test phases may be performed simultaneously. The measured data is combined at step 520 in a data processing module. At step 530, the data are analysed in the data processing module and are compared with calibration data held in database 540. The results of this analysis may be used to directly classify (step 550) the test object, for example indicating that it is suitable or unsuitable for a particular application. Alternatively, the classification step 550 may be based on a report at step 560. The report may be written to a database at step 570. In addition, at step 580, a display may be generated from the report, for display to a user. The user, who may be an expert in non-destructive testing and NDT test data interpretation, may classify the test objects based on his or hers interpretation of the data. Alternatively, the expert user may confirm or verify an automatic classification performed by the system. The results of the classification may be stored along with the report data and details of the test object or wellbore installation tested.

Figure 6:
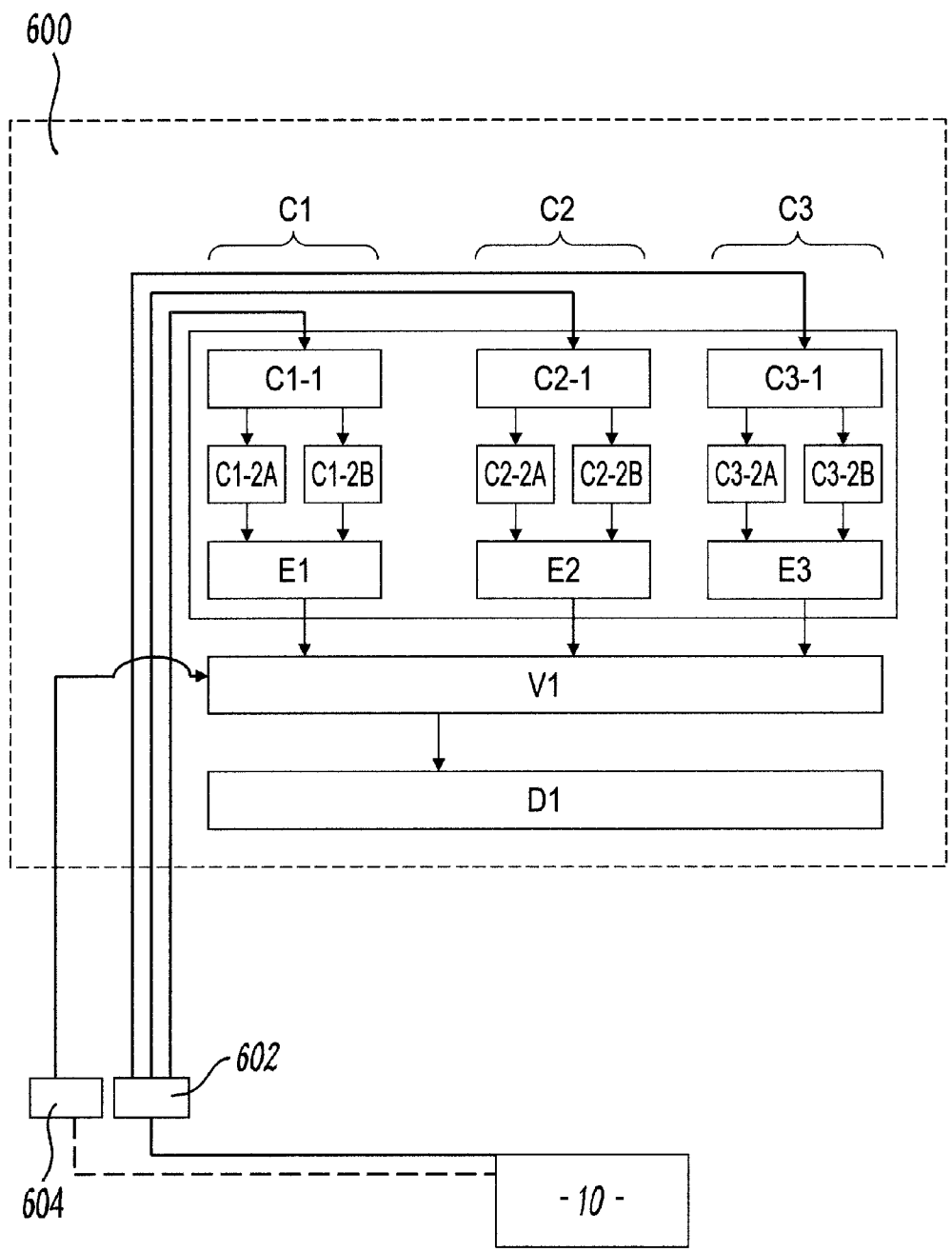
FIG. 6 is block diagram of a processing system in accordance with an embodiment of the invention.
Figure 7:
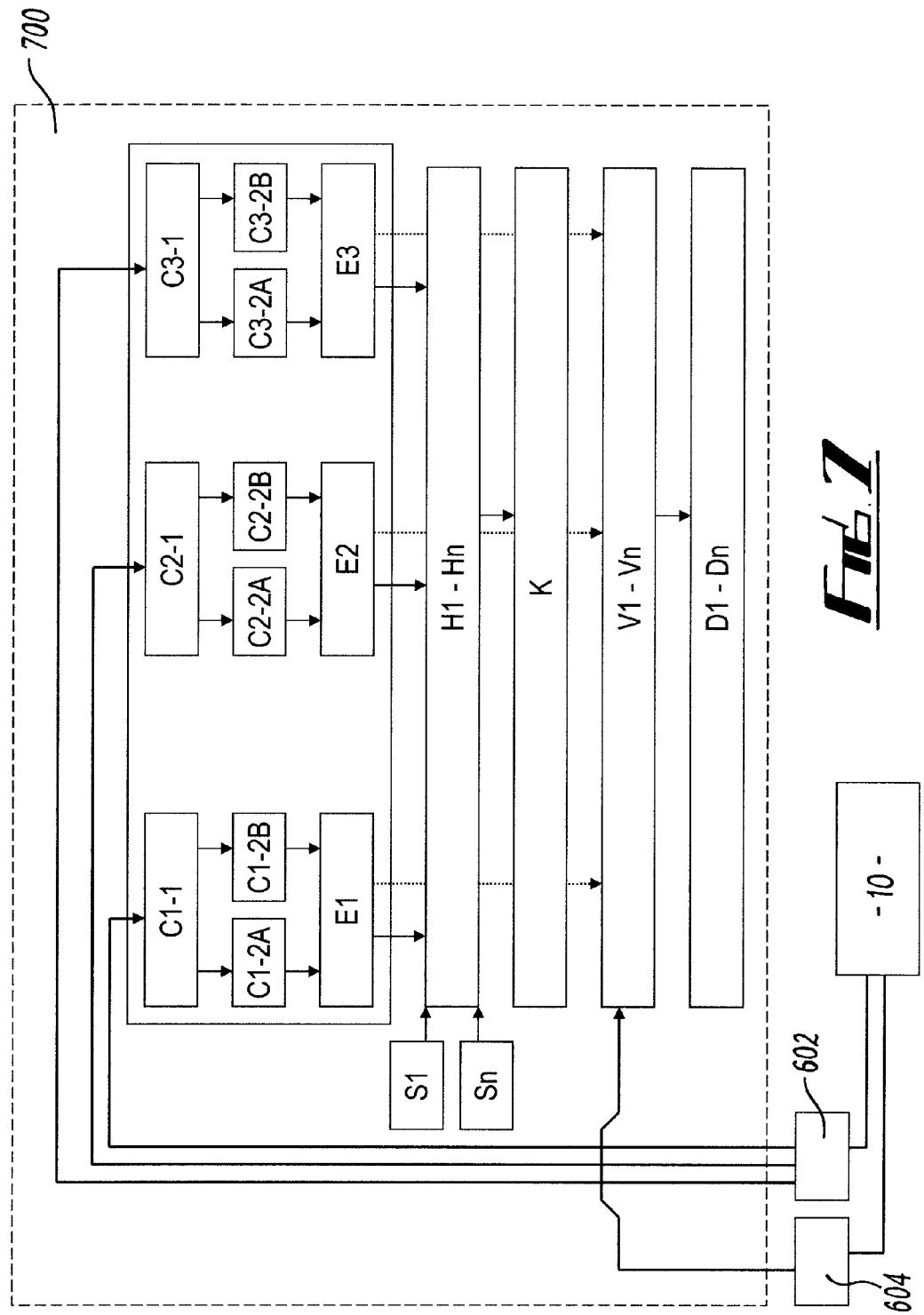
FIG. 7 is block diagram of a processing system in accordance with an alternative embodiment of the invention.

FIGS. 6 and 7 are flow charts which show the processing of the measurement data according to example embodiments of the invention. In these embodiments, the data processing module is located at surface in a dedicated apparatus, and is configured to receive the data transmitted through the umbilical 12. In alternative embodiments, the data processing module may be implemented in software running on a personal computer. Other alternatives, a part or all of the data processing may be performed in a downhole data processing module which forms part of the tool system.

In the example of FIG. 6, the measurement data are received in the data processing module 600 from the fibre optic interface and multiplexer 602. In step C1-1 the partial saturation eddy current measurement data are received in the data processing module 600, and the signal phase (step C1-2A) and the signal amplitude (step C1-2B) are evaluated individually. The analysing algorithm uses in step C1-2A the signal phase to characterise a type of event which has been detected in the wall of the tubular, and uses in step C1-2B signal amplitude as a representation of the order of magnitude of a detected event. The results are indicated at evaluation step E1.

In step C2-1, the remote field eddy current testing measurements data are received in the data processing module 600. The signal phase is analysed at step C2-2A to evaluate wall loss in the absolute mode of operation. The signal amplitude is analysed at step C2-2B to indicate defect volume. The results are indicated at evaluation step E2.

In process C3, the measurement data from the conventional eddy current testing are received (Step C3-1) and the signal phase (in C3-2A) and the signal amplitude (in C3-2B) are analysed and separately evaluated (step E3). In a similar manner to the process C1, the analysing algorithm uses the signal phase to characterise a detected event in the wall of the tubular, and in step C3-2B signal amplitude is used as a representation of the magnitude of the event. The results are indicated at evaluation E3.

The evaluation of the data from processes C1, C2 and C3 is performed at the same position P (or borehole depth) to allow a comparison of the common analysis of the detected defects and condition. The depth information is received from the sheave encoder 604. This comparison takes place at step V1, and may be used directly to provide an assessment of the condition of the test object. The result of the comparison is recorded in data storage means at step D1.

An alternative processing method is shown schematically in FIG. 7 of the drawings, and is also carried out while using the tool system 100 of FIGS. 1, 2 and 3 in data processing module 700. The embodiment of FIG. 7 is similar to that of FIG. 6, with like steps indicated with like reference numerals. However, the embodiment of FIG. 7 differs in that provision is made for an additional evaluation of the tubular by the use of predetermined quality criteria which are preset into the system as analysis thresholds. An appropriate number of analysis thresholds S1 to Sn are preset in the data processing module 700. At step H1 to Hn, the evaluation results E1, E2 and E3 are compared with the analysis thresholds. A signal indication is output at step K, for example if the analysis threshold has been exceeded, and indicates that the test object should be rejected. In step V1-Vn, a visual indication is presented to an operator, and step D1 to Dn, the analysis results are recorded in a data storage module. In this embodiment, the results of the evaluation steps E1-E3 may optionally be visually (and/or audibly) presented to the operator at steps V1-Vn.

In the method of FIG. 7, the tool system is calibrated before use, by using calibrating test objects. These calibrating test objects are of substantially the same dimensions and materials as the components used in the wellbore tubular being inspected. The calibration test objects comprise artificially-produced instances of damage to the material with known dimensions. In a preferred embodiment, the calibration defects are made according to international standards, such as the specifications of the American Petroleum Institute (API). The test defects may for example be produced by spark erosion, machining or drilling. By using calibrated test objects, the sensitivity of the tool system to the kind of defects which are typically encountered can be verified. After calibration to the API standards, the tool system may be used in testing of wellbore tubular systems according to the methods described here.

The present invention provides an improved apparatus and method for the non-destructive testing of components, including tubular components used in the oil and gas exploration and production industries. The invention has particular application to the inspection of wellbore tubulars while in situ, in downhole installations.

The invention is able to differentiate between signals from inner and outer surfaces of tubular being inspected, and is capable of detecting general wall loss, local defects, damage to connectors or couplings, and analysing coating thickness.

With the combination of features according to embodiments of the invention, the system allows a distinction between different events, i.e. between damage of different types; a higher sensitivity of testing for detecting very small damage areas, and; a clearer classification of different flaws and thus an improved definition of the boundary between the rejection and acceptance of a test component is achieved.

The invention provides a method and apparatus for the non-destructive testing of electrically conductive components such as wellbore tubulars, which is suitable for testing the components in situ a wellbore installation. The method comprises the steps of performing a remote field eddy current test phase and at least one of a conventional eddy current test phase and a partial saturation eddy current test phase. A measurement data set from each of the test phases is obtained and the combined measurement data is processed to evaluate a condition of the test component.

The invention extends to variations to the example embodiments described herein, and combinations of features other than those expressly claimed here are within the scope of the invention.

The invention claimed is:

1. A method for the non-destructive testing of electrically conductive components, the method comprising the steps of:
performing a remote field eddy current test phase on a test component;
performing a partial saturation eddy current test phase on a test component, wherein during the partial saturation eddy current test phase a variable magnet partially saturates the test component;
obtaining a measurement data set from each of the test phases, each measurement data set comprising measurement data corresponding to a plurality of test positions;
combining the measurement data sets in a data processing module and processing the combined measurement data together in the data processing module to evaluate a condition of the test component.

2. The method as claimed in claim 1, wherein the test component is wellbore tubular in a wellbore installation.

3. The method as claimed in claim 2, wherein at least part of the wellbore installation comprises a lining or coating on an inner surface.

4. The method as claimed in claim 3, wherein at least part of the wellbore installation comprises a lining of electrically insulating material.

5. The method as claimed in claim 1, further comprising the step of providing an inspection tool in a wellbore installation, and performing the test phases using the inspection tool.

6. The method as claimed in claim 5, wherein the inspection tool is deployed on an umbilical.

7. The method as claimed in claim 6, comprising the additional step of transmitting measurement data from the inspection tool to a surface from which the inspection tool is deployed via the umbilical.

8. The method as claimed in claim 1, wherein the step of combining the measurement data is performed in a data processing module at a surface from which the inspection tool is deployed.

9. The method as claimed in claim 1, comprising the step of performing the remote field eddy current test phase in an absolute mode.

10. The method as claimed in claim 1, comprising the step of performing the remote field eddy current test phase in a differential mode.

11. The method as claimed in claim 1, comprising the step of performing the partial saturation eddy current test phase in an absolute mode.

12. The method as claimed in claim 1, comprising the step of performing the partial saturation eddy current test phase in a differential mode.

13. The method as claimed in claim 1, comprising the additional step of selecting or rejecting the test component for further use according to the evaluated condition.

14. The method as claimed in claim 1, wherein the total number of defects identified in the combined measurement data is used when evaluating the condition of the test component.

15. The method as claimed in claim 1, wherein two test phases are performed simultaneously.

16. The method as claimed in claim 1, wherein the method further comprises the step of performing a conventional eddy current test phase on the test component.

17. A method for the non-destructive testing of tubular components made of electrically conductive material, the method comprising the steps of:
deploying an inspection tool system in a pipeline system, the inspection tool system comprising a remote field eddy current testing apparatus and a partial saturation eddy current testing apparatus, and;
performing at least a first test phase using the remote field eddy current testing apparatus and at least a second test phase using the partial saturation eddy current testing apparatus on the pipeline system during a single trip of the inspection tool system, wherein during the test phase using the partial saturation eddy current testing apparatus a variable magnet partially saturates the tested pipeline system.

18. A method for the non-destructive testing of tubular components made of electrically conductive material as claimed in claim 17 wherein the inspection tool comprises a conventional eddy current testing apparatus.

19. A method of processing measurement data from an inspection tool system, the method comprising the steps of:
   receiving measurement data sets from at least a remote field eddy current test phase and a partial saturation eddy current test phase performed on a test component,
      wherein during the partial saturation eddy current test phase a variable magnet partially saturates the test component;
   combining the measurement data sets obtained from the test phases;
   processing the combined measurement data together in a data processing module to evaluate a condition of the test component.

20. A method of processing measurement data from an inspection tool system as claimed in claim 19 wherein the method further comprises receiving measurement data sets from a conventional eddy current test phase performed on the test component.

21. A tool system for the non-destructive testing of test components, the tool system comprising a remote field eddy current testing apparatus and a partial saturation eddy current testing apparatus, and a data processing module configured to process combined data from at least two measurement data sets obtained from the remote field eddy current testing apparatus and the partial saturation eddy current testing apparatus, wherein the partial saturation eddy current testing apparatus includes a variable magnet configured partially saturate a test component.

22. A tool system as claimed in claim 21 wherein the tool system further comprises a conventional eddy current testing apparatus.

* * * * *